United States Patent
Sullivan et al.

(10) Patent No.: US 12,428,220 B2
(45) Date of Patent: Sep. 30, 2025

(54) WASTE CONTAINER AND METHODS OF USE

(71) Applicant: Kimberly-Clark Worldwide, Inc., Neenah, WI (US)

(72) Inventors: Shawn J. Sullivan, Neenah, WI (US); David Koenig, Menasha, WI (US); Jonathan D. Boulos, Appleton, WI (US); Andrew Long, Appleton, WI (US); Nickolas Barnes, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 136 days.

(21) Appl. No.: 18/246,758

(22) PCT Filed: Sep. 17, 2021

(86) PCT No.: PCT/US2021/050875
§ 371 (c)(1),
(2) Date: Mar. 27, 2023

(87) PCT Pub. No.: WO2022/093424
PCT Pub. Date: May 5, 2022

(65) Prior Publication Data
US 2023/0365328 A1 Nov. 16, 2023

Related U.S. Application Data

(60) Provisional application No. 63/107,081, filed on Oct. 29, 2020.

(51) Int. Cl.
*B65F 1/00* (2006.01)
*B65F 1/16* (2006.01)
(Continued)

(52) U.S. Cl.
CPC ............... *B65F 1/004* (2013.01); *B65F 1/16* (2013.01); *G01N 33/497* (2013.01);
(Continued)

(58) Field of Classification Search
None
See application file for complete search history.

(56) References Cited

U.S. PATENT DOCUMENTS 4,546,502 A * 10/1985 Lew ..................... A47K 11/02
4/111.1
2004/0100376 A1 5/2004 Lye et al.
(Continued)

FOREIGN PATENT DOCUMENTS

WO WO2019135232 7/2019

OTHER PUBLICATIONS

International Search Report and Written Opinion for PCT/US2021/050875 for PCT/US2021/050875 dated Jan. 18, 2022, 9 pages.

*Primary Examiner* — John F Mortell
(74) *Attorney, Agent, or Firm* — Dority & Manning, P.A.

(57) ABSTRACT

Waste storage devices are provided. The waste storage device is capable of sharing information concerning the health of a user. The waste storage device includes a sampling area in the interior of the container configured to detect the presence of one or more volatile organic compounds. The waste storage device is in communication with a server system capable of generating and delivering a notification to a user. Methods for communicating a health state of a user are also provided.

19 Claims, 8 Drawing Sheets

(51) Int. Cl.
  *G01N 33/497*   (2006.01)
  *G16H 40/67*    (2018.01)
(52) U.S. Cl.
  CPC ........ *G16H 40/67* (2018.01); *B65F 2210/102* (2013.01); *B65F 2210/128* (2013.01); *B65F 2210/167* (2013.01); *B65F 2210/168* (2013.01); *B65F 2210/20* (2013.01); *B65F 2240/132* (2013.01); *G01N 33/4975* (2024.05)

(56) References Cited

U.S. PATENT DOCUMENTS

| | | | | |
|---|---|---|---|---|
| 2014/0278630 | A1* | 9/2014 | Gates | G06Q 10/047 |
| | | | | 705/7.13 |
| 2014/0379588 | A1* | 12/2014 | Gates | G06T 7/0008 |
| | | | | 705/308 |
| 2016/0300297 | A1* | 10/2016 | Kekalainen | G06F 17/18 |
| 2017/0090447 | A1* | 3/2017 | Skocypec | B65F 1/04 |
| 2018/0292381 | A1* | 10/2018 | Faybishenko | B65F 1/1623 |
| 2021/0375456 | A1* | 12/2021 | Kurfirst | G16H 40/67 |
| 2022/0120724 | A1 | 4/2022 | Sharman et al. | |

\* cited by examiner

WASTE CONTAINER AND METHODS OF USE

RELATED APPLICATIONS

The present application is the national stage entry of International Patent Application No. PCT/US2021/050875 having a filing date of Sep. 17, 2021, and Provisional Patent Application No. 63/107,081 having a filing date of Oct. 29, 2020, which is incorporated herein in its entirety by reference thereto.

BACKGROUND

Waste storage devices, particularly diaper pails and diaper disposal containers, are known. These products typically house used diapers in a sealed or semi-sealed fashion such that odorous compounds emitted from the used diapers do not invade the ambient atmosphere surrounding the waste storage device. Accordingly, such devices reduce odor in bathrooms and/or bedrooms in which they are disposed. These devices can be equipped with odor masking devices or compounds and/or odor eliminated devices and/or compounds. Many such odor masking or odor eliminating devices include mechanisms capable of reducing compounds, such as volatile organic compounds, that are emitted from the waste. The mechanisms for eliminating or masking compounds emitted from waste are wide and varied.

Further, many devices have been developed that can alert caretakers to certain health conditions of users. For example, sensors can be utilized to detect body temperature, oxygen levels, etc. that allow for caretakers or healthcare professionals to attend to the health needs of the pediatric subject. However, despite certain device advances, there ceases to be an everyday usable waste storage device that is capable of detecting biological information from a subject, analyzing said information, and generating and transmitting a message to the caretaker regarding the health or disease state of the pediatric subject.

In view of the above, a need exists for a waste container capable of detecting and transmitting the health state of a user, such as a pediatric subject, to a caretaker such that healthy states, chronic disease states, and/or acute disease states can be more easily detected and subsequently treated.

SUMMARY

In general, the present disclosure is directed to a waste storage device configured to share information concerning the health of a user. The waste storage device includes a container comprising a top portion, a bottom portion, a side portion and a lid attached to the top portion of the container defining an interior space configured to receive waste; a sampling area formed in the interior space of the container, the sampling area configured with one or more sensors configured to detect the presence of one or more volatile organic compounds; and a server system in communication with the one or more sensors, wherein the server system is configured to deliver a notification based, at least in part, on data provided by the one or more sensors.

In another embodiment, provided is a method for communicating a health state of a user. The method includes obtaining, by one or more computing devices, data from one or more sensors in a sampling area, the sampling area housed in a container configured to hold waste; determining, by the one or more computing devices, a health state of a first user based, at least in part, on the data obtained from the one or more sensors; and providing, by the one or more computing devices, a notification, indicative that health state information of the first user is available to one or more peripheral devices.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

The present disclosure is generally directed to a waste storage device for communicating information regarding the health of a user. The waste storage device includes a container comprising a top portion, a bottom a bottom portion, a side portion and a lid attached to the top portion of the container defining an interior space configured to receive waste; a sampling area formed in the interior space of the container, the sampling area configured with one or more sensors configured to detect the presence of one or more volatile organic compounds; and a server system in communication with the one or more sensors, wherein the server system is configured to deliver a notification based, at least in part, on data provided by the one or more sensors.

FIGS. 1-4 illustrate exemplary waste storage containers 10 according to example embodiments of the present disclosure. As shown, the waste storage container 10 includes a top portion 12, a bottom portion 14, a side portion 16, and a lid 18 attached along at least a portion of the top portion 12 of the container 10. The container 10 defines an interior space 20 that is configured to receive waste 22. The top portion 12 of the container 10 can include an opening 23 such that the interior space 20 of the container is accessible when the lid 18 is in an open position. As such, when the lid 18 is in a closed position, the opening 23 and, subsequently the interior space 20, of the container 10 is not accessible. Advantageously, the lid 18 can be configured such that when it is in a closed position the interior space 20 of the container is sealed off from the surrounding ambient environment. In certain embodiments, the lid 18 can be hingedly attached to the top portion 12 of the container 10. In embodiments, the side portion 16 can include a plurality of sidewalls configured to form any shape container 10, such as a rectangular or square container. In other embodiments, the side portion 16 can include a continuous sidewall capable of forming a container 10 having a circular or ovular shape. The side portion 16 can be configured in a multitude of dimensions depending on the desired footprint for the container 10.

The container 10 includes a sampling area 24 disposed in the interior space 20 of the container 10. For example, in certain embodiments sampling area 24 takes up less than 100% of the volume of the interior space 20. For example, the sampling area 24 can include from about 60 volume % to about 20 volume % of the interior space 20 of the container 10. The volume size of the sampling area 24 in the interior space 20 should be sized such that it is capable of receiving and holding one or more pieces of waste 22 when the lid 18 is in a closed position. In embodiments, the sampling area 24 is formed between the lid 18 in closed position and a discarding mechanism 28. Accordingly, the sampling area 24 can be completely sealed off from the ambient environment via the lid 18 and the remainder of the interior space 20 via the discarding mechanism 28. Accordingly, when the lid 18 is in a closed position, the sampling area 24 can include a headspace 26 surrounding the waste 22. One or more volatile organic compounds (VOCs) 30 can be emitted by the waste 22 into the headspace 26 of the sampling area 24.

The container 10 includes one or more sensors 32 configured to detect the presence of one or more VOCs 30 in the headspace 26 of the sampling area 24. Sensors 32 capable of measuring VOCs in gas phase are known. For example, certain sensors utilize one or more electrodes in order to measure change of current or voltage generated between electrodes due to reduction or oxidation of VOCs. Indeed, sensors 32 can generate sensor signals based upon the current or voltage change between a primary electrode and a reference electrode. Such, sensor signals can then be analyzed via a suitable processor system in order to determine the composition of VOCs in the sampling area 24, including the specific chemical compositions of the VOCs and the amounts of each VOC present in the headspace. Such detection and analyzation of the VOCs can be further analyzed to determine the health state of the subject individual from whom the waste is produced as will be discussed further herein.

In certain embodiments, the sampling area 24 can include one or more humidity controlling devices 34. For example, the humidity controlling device 34 can include any suitable desiccant material capable of absorbing and trapping humidity from the headspace 26 of the sampling area 24. The humidity controlling device 34 can include a permeable patch or container containing desiccant material. The patch or container can include an outer membrane that is permeable to water vapor within the headspace 26, such that water vapor can enter the patch or container and is trapped by the desiccant material located therein. Any suitable desiccant material can be used in the sampling area 24 provided herein. Example desiccant materials include solid desiccant materials such as silica gel, zeolites, activated alumina, synthetic polymers, and combinations thereof. Without being bound by any particular theory, inclusion of the humidity controlling device 34 can improve the accuracy of the one or more sensors 32. For example, water vapor can interfere with electrical signals experienced by the electrodes in the sensor 32, which can affect accurate detection of the VOCs 30.

The interior space 20 further comprises a discard area 36 for holding waste 22 that has been discarded from the sampling area 24. One or more pieces of waste 22 can be stored in the discard area 36 for a desired period of time. The discard area 36 can include a flexible, plastic liner, such as a trash bag or trash liner, that can hold waste 22 in the discard area 36. In such embodiments, the plastic liner containing the waste 22 can be removed from the discard area 36, once full. Similar to other known products, the discard area 36 can be equipped with desiccants, odor-eliminating devices, odor-masking devices, etc. in order to reduce odor from the waste 22 in the discard area 36.

Figure 1:
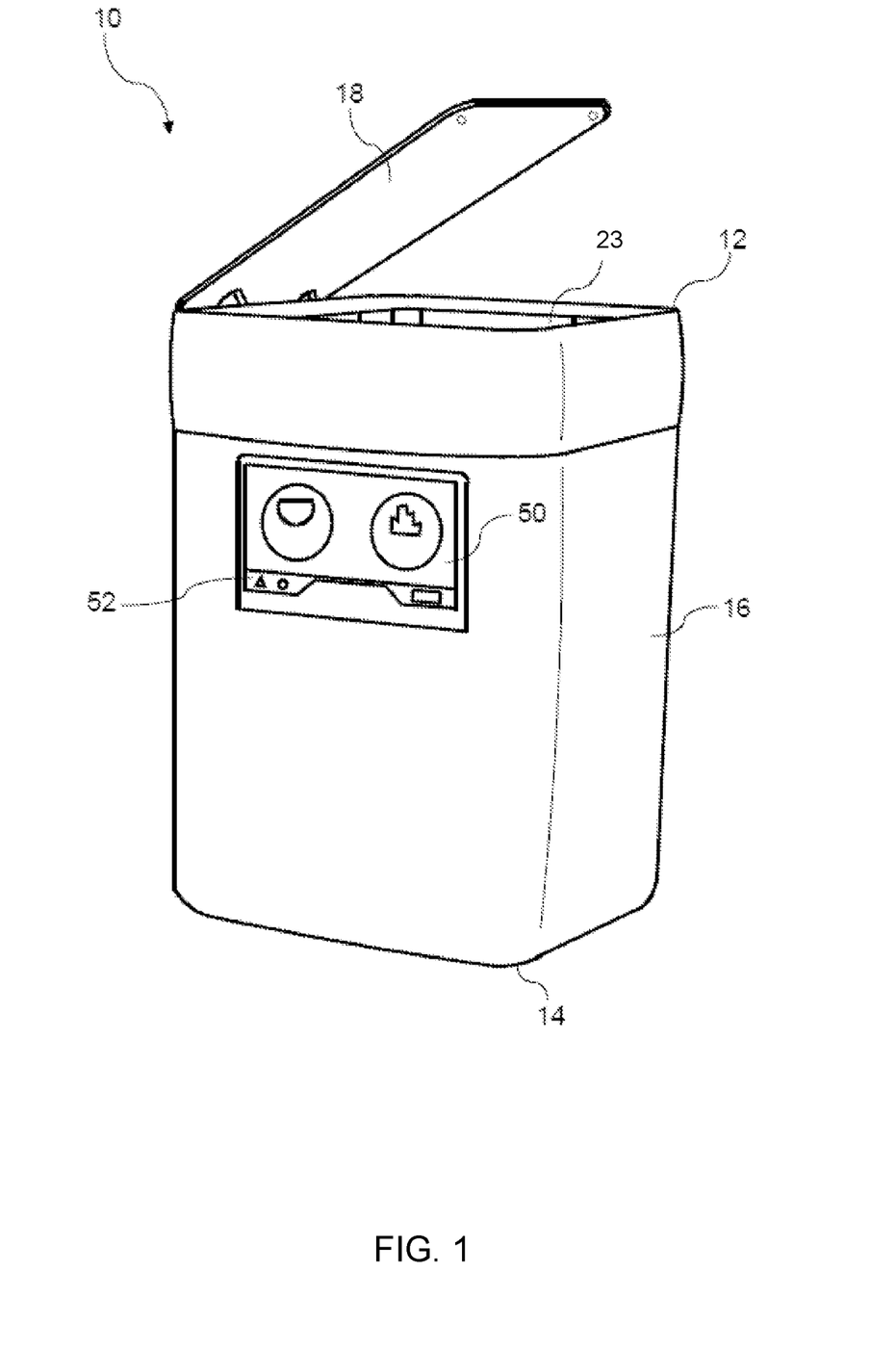
FIG. 1 illustrates a perspective view of a waste disposal container according to example embodiments of the present disclosure.
Figure 2:
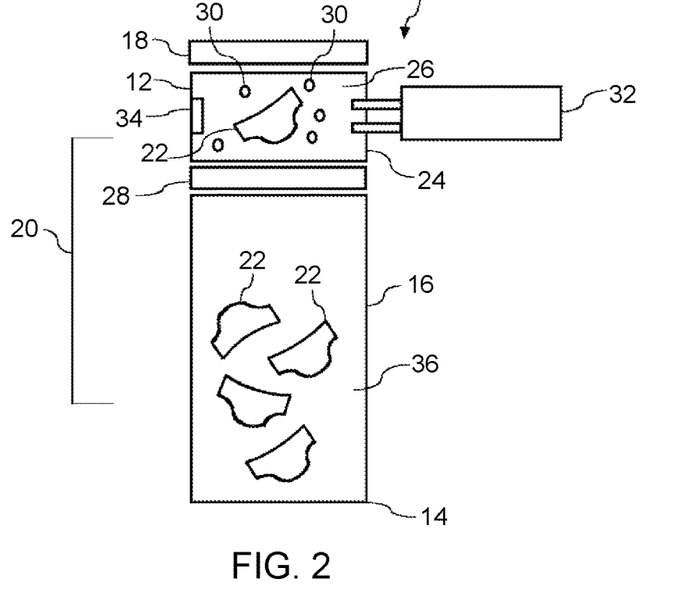
FIG. 2 illustrates a cross-sectional schematic view of a waste disposal container according to example embodiments of the present disclosure.
Figure 3:
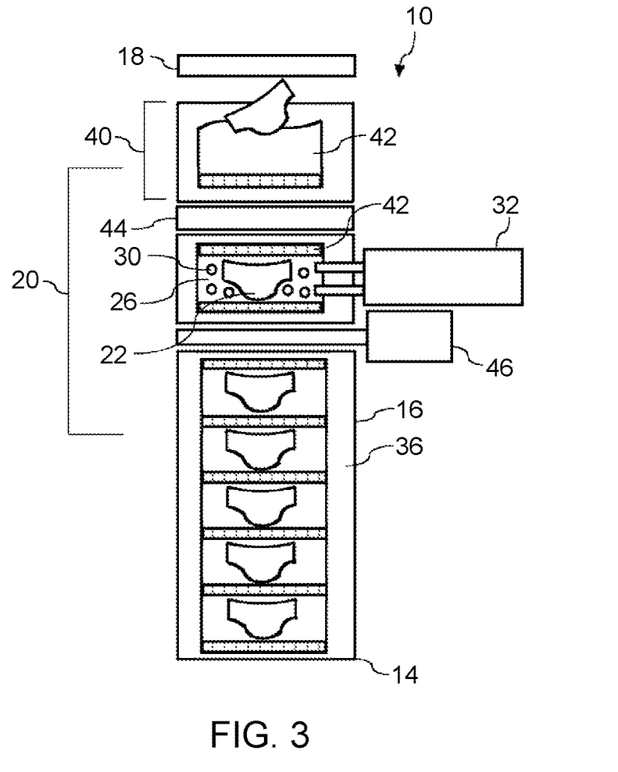
FIG. 3 illustrates a cross-sectional schematic view of a waste disposal container according to example embodiments of the present disclosure.

Now referring to FIG. 3, in certain embodiments a staging area 40 is provided in the interior space 20. In embodiments, the staging area 40 can be provided between the lid 18 and the sampling area 24. The staging area 40 is configured such that a sealed packet of waste 42 can be formed in the staging area 40. For example, one or more pouches 42 can be disposed in the staging area 40. The waste 22 can be placed in the pouch 42 and sealed forming a sealed packet of waste 42. In certain embodiments, the staging area 40 and the sampling area 24 are separated by a sealing mechanism 44 capable of sealing one or more open ends of the pouch 42. The sealing mechanism 44 is disposed in the interior of the container such that the sampling area 24 is sealed off from the staging area 40. Once the sealed packet of waste 42 is formed in the staging area 40, it can be moved to the sampling area 24. In such embodiments, the headspace 26 is formed in the interior of the sealed packet of waste 42. Also, VOCs 30 released from the waste 22 are contained within the sealed packet 42. One or more sensors 32 can access the headspace 26 in the sealed packet 42 in order to detect VOCs 30 contained therein. In such embodiments, the discarding mechanism 28 can also include a drive mechanism 46 located between the sampling area 24 and the discard area 36. After VOC detection by the sensor 32 is complete, the drive mechanism 46 is operably configured to move the sealed packet of waste 42 to the discard area 36. Further, the drive mechanism 46 is disposed in the interior space such that the sampling area 24 can be sealed off from the discard area 36. In such embodiments, sealed packets of waste 42 are stored in the discard area 36 until they are removed by a user.

Figure 4:
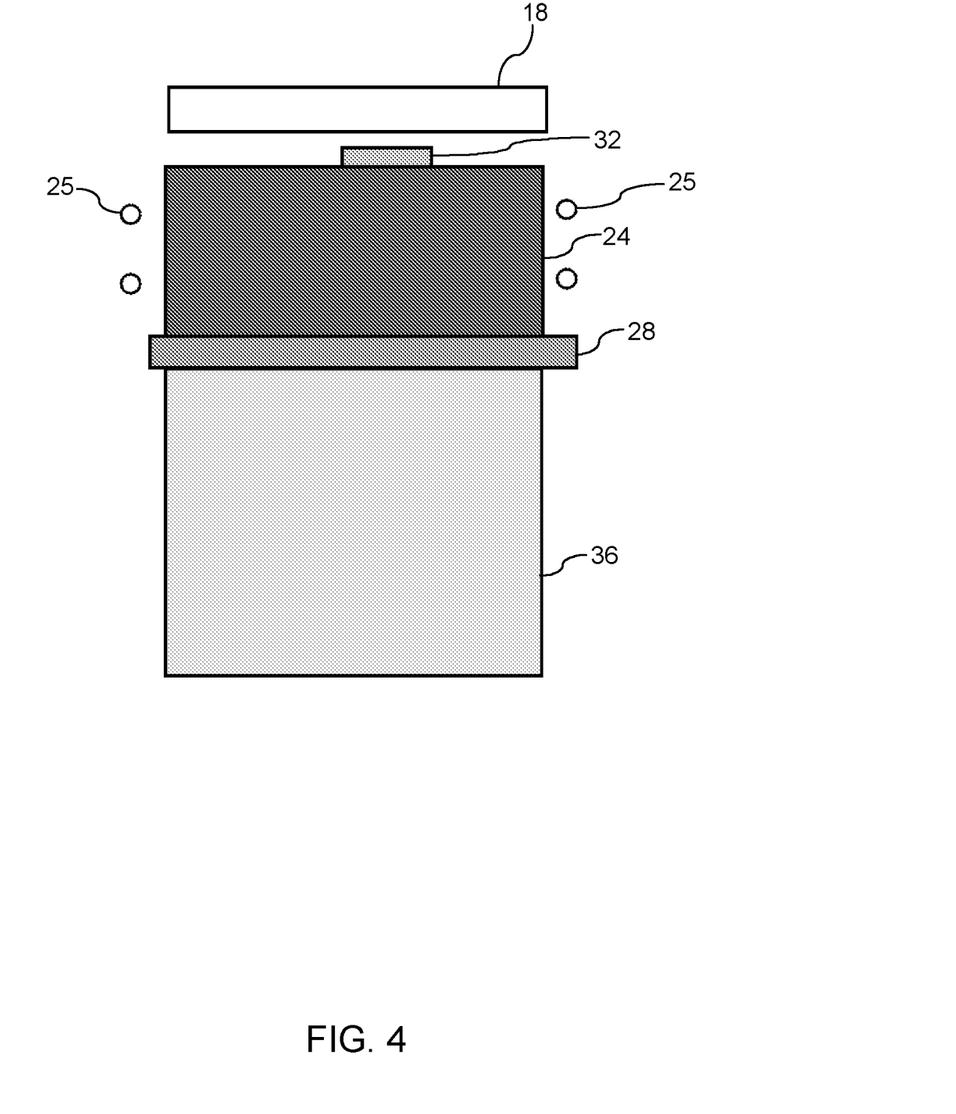
FIG. 4 illustrates a cross-sectional schematic view of a waste disposal container according to example embodiments of the present disclosure.

In certain embodiments, as shown in FIG. 4, one or more sensors 32 can be disposed between the lid 18 and a topside of the sampling area 24. In such embodiments, one or more heating elements 25 may be disposed on or around the sampling area 24, such that the waste 22 contained within the sampling area 24 can be heated to facilitate release of VOCs 30 into the headspace 26 of the sampling area 24. Such a configuration of the sensor 32 in combination with heating the waste 22 can speed release of VOCs 30 from the waste 22 for more rapid detection and analysis. The heating element 25 can include heating coils, jackets, etc.

In certain embodiments, the sampling area 24 can include one or more purge mechanisms configured to purge gases from the headspace 26 of the sampling area 24. (Not shown). Suitable purge mechanisms can include gases valves capable of having an open position for releasing gases from the headspace 26 to the ambient environment surrounding the container 10 and a closed position for sealing off the headspace 26 from the ambient environment. Additionally, the sampling area 24 can be equipped with vacuum pumps or valves for controlling the pressure in the sampling area 24.

The waste 22 can include any absorbent article having bodily extrudate contained therein. For example, the absorbent article can include diapers, incontinence articles, and/or feminine care articles. The bodily extrudate can include urine, fecal matter, and/or menorrhea.

In embodiments, the container 10 can include a display device 50 capable of displaying a notification or message. For example, the display device 50 can be located on an outer surface of the container 10, such as on one of the side portions 16 of the container 10. In other embodiments, the display device 50 can be located on the lid 18 of the container 10. The display device 50 can be located anywhere on the container 10 such that it is easily viewable by a user. The display device is capable of displaying a notification generated by a server system 70 or computing device 330 as will be further discussed hereinbelow. The display device 50 can also include one or more user interfaces 52, such that data provided by the user through the user interface 52 can be communicated to one or more computing devices 330 or server systems 70. Additionally, the user interface 52 can, in some implementations, present a list of a plurality of predefined action to facilitate user interaction with the container 10. Such predefined actions can include instructing the container 10 that waste has been provided in the sampling area 24, instructing the sensors 32 to begin detection, or to instruct the container 10 to discard the waste 22 from the sampling area 24 to the discard area 36. Other predefined actions can be included in the list as necessary or desired by the user. In some implementations, a user can interact with a user interface implemented on, for instance, one or more computing devices 330 (e.g., smartphone, tablet, etc.) to provide data indicative of the user's health or other user identifying data.

Figure 5:
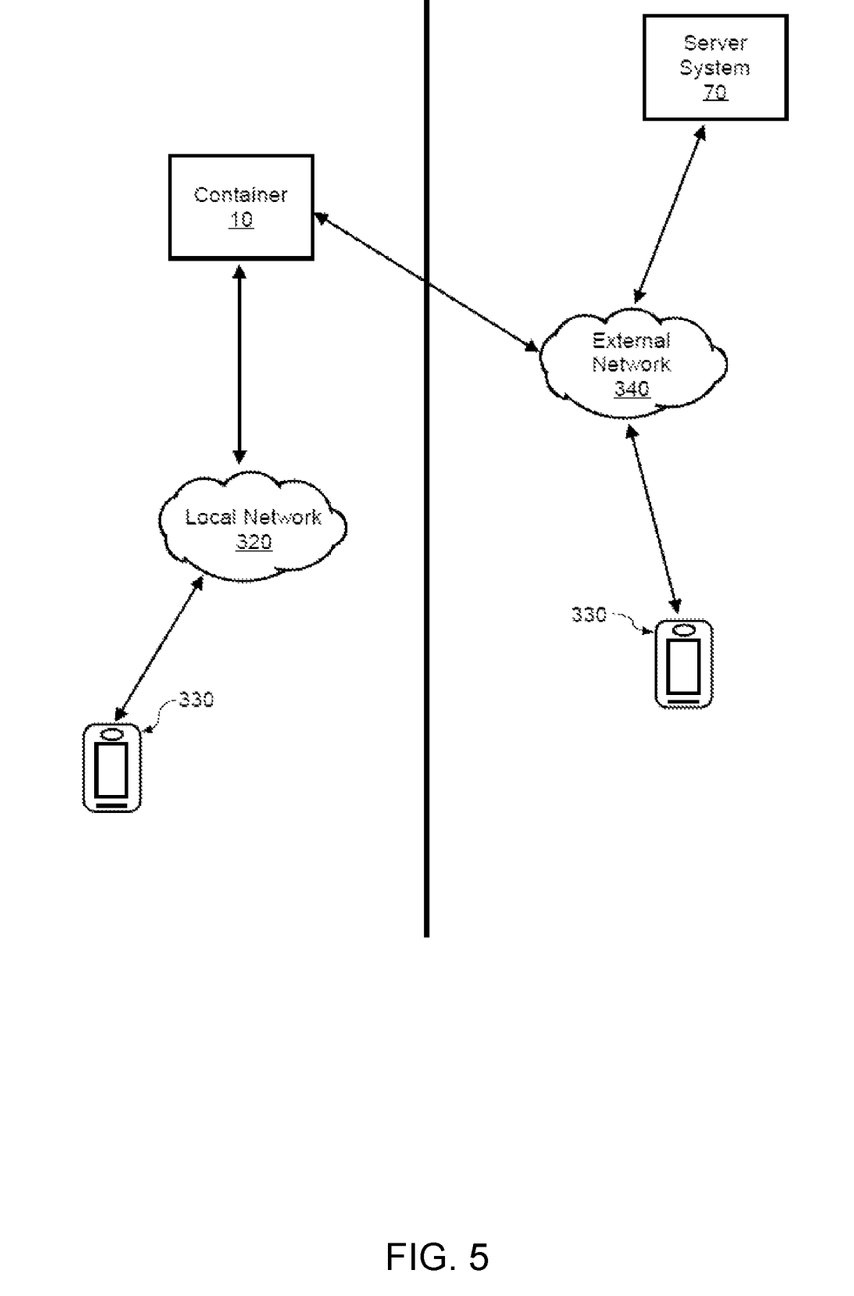
FIG. 5 illustrates a system for providing communication between the waste disposal container and other devices according to example embodiments of the present disclosure.
Figure 6:
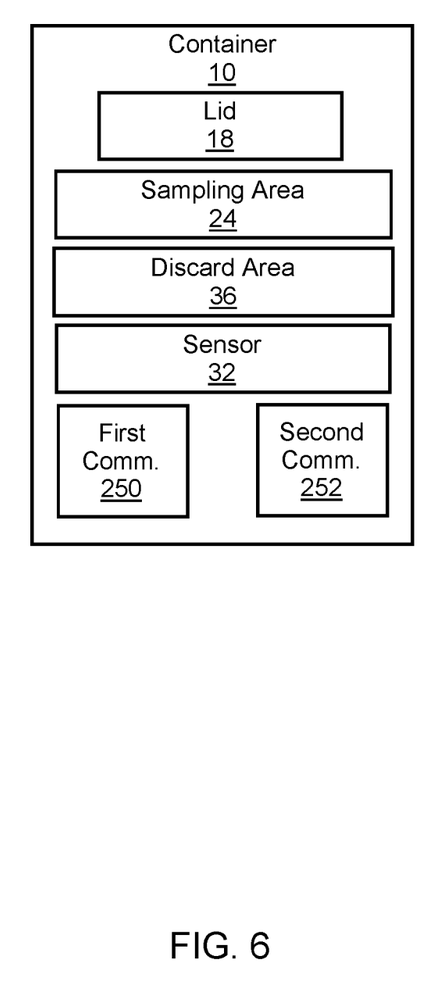
FIG. 6 illustrates a block diagram of components of the waste disposal container according to example embodiments of the present disclosure.

Referring now to FIGS. 5-6, the container 10 can be configured to communicate over a local network 320 with one or more devices, such as a computing device 330. The container 10 can further include a first communication interface 250 configured to provide communication between the container 10, including the one or more sensors 32, and one or more devices, e.g., computing devices 330 over a local network. For instance, in certain implementations the local network can be a Bluetooth network. In this manner, the container 10 can be in communication with one or more Bluetooth-enabled devices over the Bluetooth network. In some implementations, the local network can be a WiFi network. In this manner, the container 10 can communicate with one or more Wifi-enabled devices over the WiFi network. In some implementations, the local network can be a LoRa network. In this manner, the container 10 can communicate with one or more LoRa-enabled devices over the LoRa network. It should be appreciated, however, that the first network can include any suitable type of local network implementing any suitable type of protocol (e.g., Bluetooth, Wifi, Lora, etc.). It should be appreciated, however, that the local network 320 can be based on any suitable wireless protocol.

In certain embodiments, however, the container 10 can be in communication with one or more remote computing devices 330 (e.g., smartphone, tablet, etc.) over an external network 340. For example, the container 10 can include a second communication interface 252 configured to provide communication between the container 10, including the sensors 32, and one or more remote computing devices 330 and/or server systems 70. In certain embodiments, the external network 340 can be based on the Wifi protocol. In certain embodiments, the second communication interface 252 can be configured to provide communications between the container 10 and one or more devices (e.g., computing devices 330 or server system 70) over a second network that is different from the first network. For example, the second network can be a WiFi network. In this manner, the container can communicate with one or more WiFi-enabled devices over the WiFi network. As another example, the second network can be a cellular network. In this manner, the container 10 can communicate with one or more cellular devices (e.g., smartphones, tablets, etc.) over the cellular network.

In addition to the networks discussed, it should be appreciated that local or external networks can be selected using any wireless protocols or communication technologies. For example, suitable wireless protocols or communication technologies used in accordance with example aspects of the present disclosure can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), Power over Ethernet, etc. Other suitable wired and/or wireless communication technologies can be used without deviating from the scope of the present disclosure.

Figure 7:
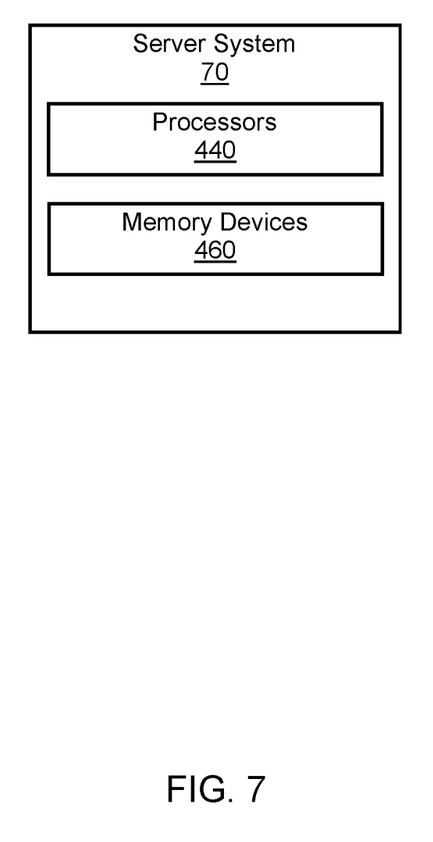
FIG. 7 illustrates a block diagram of components of a server system according to example embodiments of the present disclosure.

Referring to FIG. 7, the computing devices 330 or the container 10 can include or be connected to server systems 70 containing processors capable of analyzing data according to computer-implemented programs stored on the server system 70. The one or more processors 440 can be any suitable processing device, such as microprocessors, integrated circuits (e.g., application specific integrated circuits), field programmable gate arrays, etc. that perform operations to control components (e.g., any of the components described herein). The one or memory devices 460 can be any suitable media for storing computer-readable instructions and data. For instance, the one or more memory devices 460 can include random access memory such as dynamic random access memory (DRAM), static memory (SRAM) or other volatile memory. In addition, and/or in the alternative, the one or more memory devices can include non-volatile memory, such as ROM, PROM, EEPROM, flash memory, optical storage, magnetic storage, etc.

The one or more memory devices 460 can store computer-readable instructions that, when executed by the one or more processors 440, cause the one or more processors 440 to perform operations, such as any of the operations described herein. The instructions can be software written in any suitable programming language or can be implemented in hardware.

The one or more memory devices 460 can also store data that can be obtained, received, accessed, written, manipulated, created, and/or stored. As an example, the one or more memory devices 460 can store data associated with one or more classifier models (e.g., machine learned classifier models) that can be used to classify data obtained from one or more sensor devices (e.g., sensor 32) of the container 10. More specifically, the one or more classifier models can classify the data as being indicative of particular disease states or not indicative of particular disease states. Storing the classifier model(s) locally in the one or more memory devices 460 can allow for local processing of data obtained from the one or more sensors 32 of the container 10.

Generally, the server system 70 may include a central controller configured to receive data obtained from the one or more sensors 32, analyze data received from the one or more sensors 32, and generate one or more notifications. The server system 70 is operable to interface with the computing devices 330 or container 10 as disclosed herein for retrieval of data, generation and display of the notification described herein. The server system can be configured to implement machine-learned models and to generate metadata as part of the output of the machine-learned model.

It should be appreciated that the computing devices 330, container 10, sensors, 32 and/or display devices 50 may include similar features or may be configured with functionality to allow for an exchange of information required to function as described herein. The devices disclosed herein can include network-enabled devices and may include a number of internal components, such as a controller having a program memory, a microcontroller or microprocessor (MP), a random access memory (RAM), and an input/output (I/O) bus, all of which may be interconnected via an address or data bus. The server system may include multiple, and even redundant, program memories and random access memories to increase expandability, capacity and/or processing speed.

Figure 8:
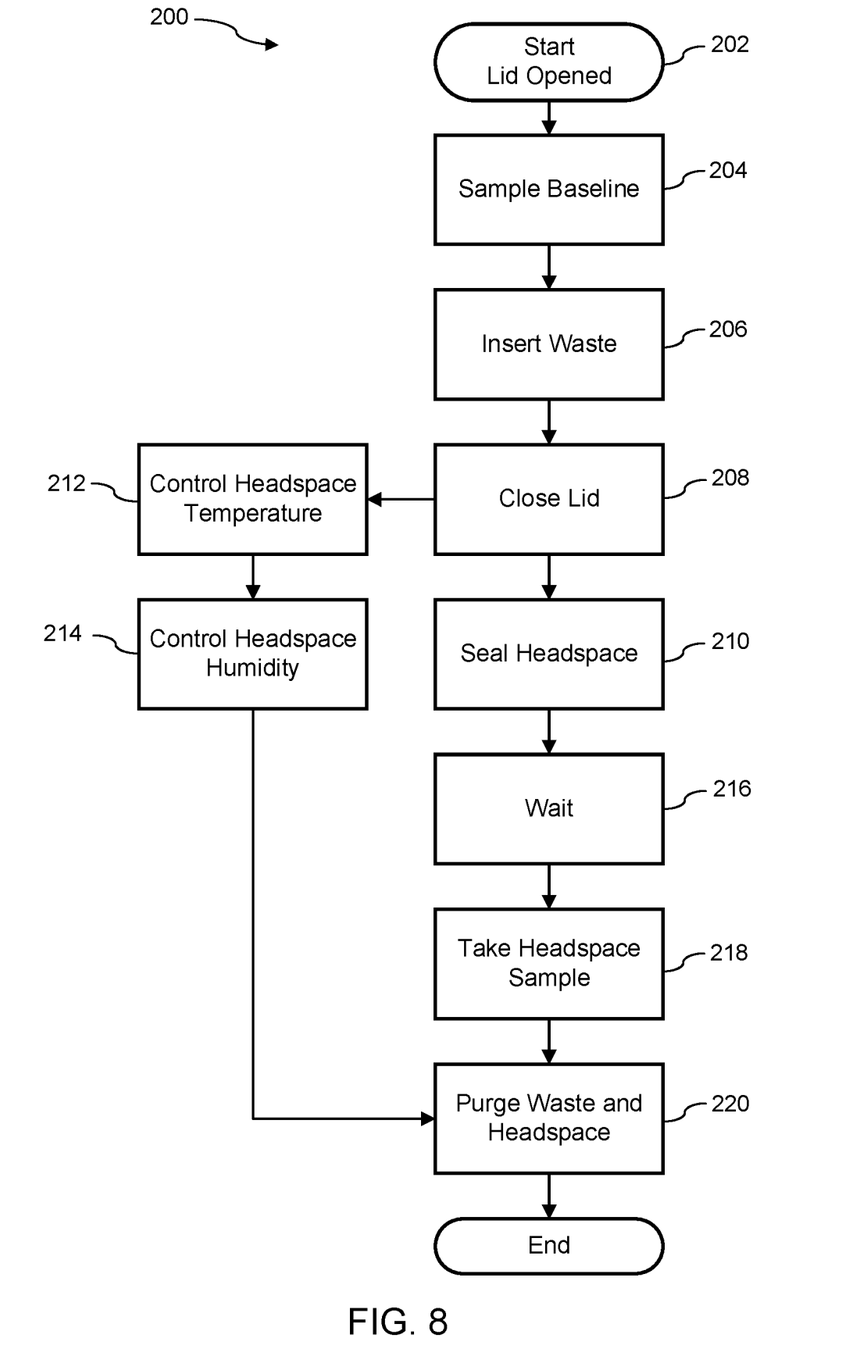
FIG. 8 illustrates a flow-chart of an example process according to one embodiment of the present disclosure and FIG. 9 illustrates a flow-chart of an example method according to example embodiments of the present disclosure.

FIG. 8 shows an exemplary process (200) for obtaining data from a waste sample. The process begins at (202) with the lid opened. For example, lid 18 should be in an open position such that interior space 20 is accessible through opening 23.

At (204) a baseline measure is taken. For example, one or more sensors 32 can be used to obtain a data sample of the sampling area 24 while the lid 18 is open. This data can be communicated via communication interface 250 to a computing device 330. The baseline sample can be stored on one or more memory devices 460.

At (206) waste is inserted into a sampling area. For example, a diaper containing a body extrudate can be inserted into the sampling area 24 through opening 23. At (208) the lid is closed. For example, lid 18 can be closed so that the interior space 20 of the container is sealed off from the surrounding ambient environment.

At (210) the headspace is sealed. For example, in some embodiments, the headspace 26 of the sampling area 24 can be completely sealed off from the ambient environment via the lid 18 and from the remainder of the interior space 20 via the discarding mechanism 28. In some embodiments, a sealing mechanism 44 can seal the headspace 26 of the sampling area 24 from a staging area 40.

At (212) the temperature of the headspace is controlled. For example, one or more heating elements 25 disposed around sampling area 24 can be used to control the temperature of the headspace 26. Additionally, a temperature sensor may be used in conjunction with a computing device 330 and the one or more heating elements 25 to create a control loop for controlling the temperature at a certain setpoint.

At (214) the humidity of the headspace is controlled. For example, a humidity controlling device 34 including a permeable patch or container containing desiccant material may be used to control the humidity of the headspace 26. Steps (208)-(214) can be performed in any suitable order or can be performed simultaneously. According to process (200) the temperature and humidity remain controlled until the waste and headspace are purged at (220), as described below.

At (216), the process allows the waste to sit in the controlled headspace for a period of time. For example, enough time should be allowed for the waste 22 to release enough VOCs 30 to perform a useful analysis of the waste. Once, this time has elapsed, at (218) a headspace sample is taken. For example, one or more sensors 32 can be used to obtain a data sample of the headspace 26 of the sampling area 24. This data can be communicated via communication interface 250 to a computing device 330. The data sample can be stored on one or more memory devices 460.

At (220) the waste and headspace are purged. For example, a valve can be opened to release gases from the headspace 26 to the ambient environment surrounding the container 10. Additionally, a discarding mechanism 28 can be used to discard the waste 22.

By taking a baseline sample prior to sampling the waste, process (200) allows for a more accurate analysis of the waste. For example, the baseline sample creates a reference point for the waste sample data to be compared to, which tends to negate the effects of external factors, such as VOCs in the ambient environment.

Figure 9:
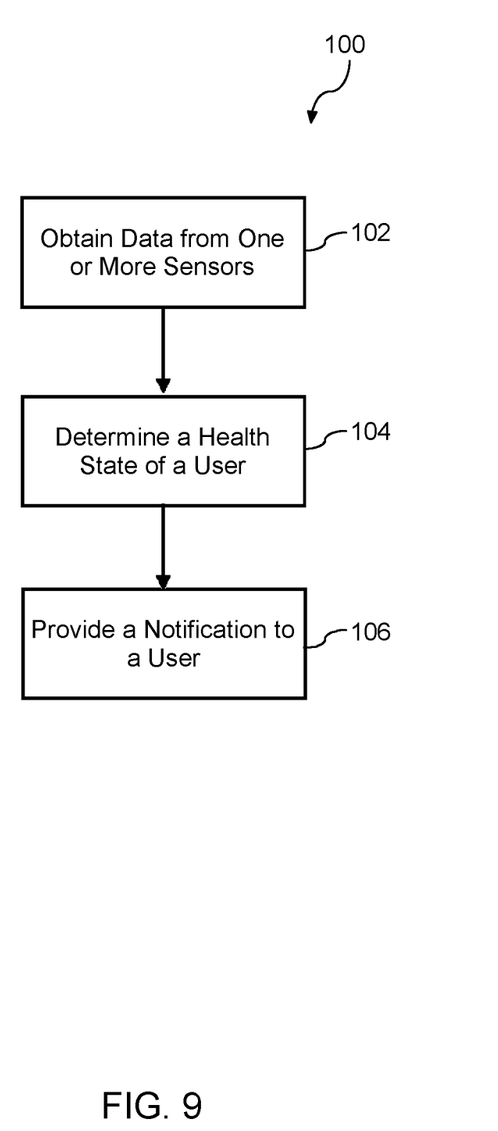

FIG. 9 shows an exemplary process (100) for communicating a health state of a user. The method of FIG. 9 will be discussed with reference to container 10 as shown in FIGS. 1-4. However, the method is not so limited and any container or number of containers capable of performing the method disclosed herein can be used. At (102) the method includes obtaining, by one or more computing devices 330, data from one or more sensors 32 in a sampling area 24, the sampling area 24 housed in the container 10 configured to hold waste 22. For example, prior to obtaining the data, a user can put waste 22 into the sampling area 24 of the container 10. The sampling area 24 can be accessed by opening the lid 18. When the lid 18 is in a closed position, the sampling area 24 is sealed off from the ambient environment. Accordingly, a headspace 26 can be created in the sampling area 24 around the waste 22. One or more VOCs 30 in the sampling area 24 can then be detected by one or more sensors 32. For example, one or more sensors 32 can be operably configured to sample the headspace 26 to detect the presence of one or more VOCs 30. One or more sensors 32 can include known sensors 32 that are capable of measuring VOCs in gas phase. Further, the humidity or water vapor content in the headspace 26 of the container 10 can be controlled, such that accurate data is obtained by the sensors 32. For example, higher levels of humidity within the headspace 26 may interfere with the sensors 32 ability to accurately detect VOCs 30. The pressure of the sampling area 24 can also be controlled according to desired processing parameters. For instance, the sampling area can be equipped with one or more vacuum valves or pumps capable of providing a vacuum pressure in the sampling area 24.

In embodiments, the data generated by the one or more sensors 32 can include one or more signals. For example, sensors 32 utilize one or more electrodes in order to measure change of current or voltage generated between electrodes due to reduction or oxidation of detected VOCs. Accordingly, sensors can generate signals based upon the current or voltage change between a primary electrode and a reference electrode. Such, signal data can then be transmitted and analyzed accordingly. For example, in certain embodiments, data from the sensors can be communicated to a computing device 330, e.g. a smartphone, via a suitable network connection as described herein. For instance, the container 10, including the sensors 32, can be a Blue-tooth connected device that is capable of exchanging data/information with one or more other Blue-tooth connected devices, e.g. a user's smartphone. In certain embodiments, the container 10 including the sensors 32 can be connected to a Wifi network and thus, is capable of communicated with other Wifi-connected devices, e.g., a user's smartphone. In such a manner, information and data can be exchanged between the user and the container 10. Further, in certain embodiments, data provided by the sensors 32 can be wirelessly communicated to a computing device 330, such as a smart-phone, which can then communicate the data to one or more other computing devices including server systems 70 capable of performing desired analysis on said data. In certain embodiments, it is also contemplated that analysis and computing can be performed on the data via the user's smartphone.

At (104) the method includes determining, by one or more computing devices, a health state of a first user based, at least in part, on data obtained from the one or more sensors. For instance, sensor data can include information regarding VOC output from the microbiota community present in the user's gastrointestinal tract. For example, the gut microbiome or microbiota generally refers to the totality of microorganisms, bacteria, viruses, protozoa, and fungi and their collective genetic material that is present in the gastrointestinal tract. The gut microbiome plays an important part in metabolism, immune, and neuroendocrine responses. The gut microbiome facilitates mineral absorption, synthesis of enzymes, vitamins, amino acids, and products of short-chain fatty acids (SCFAs). Furthermore, the organisms in the gut microbiome produce fermentation byproducts, such as acetate, propionate, and butyrate, which are all important for gut health and provide immunomodulation and protection against pathogens. Depending on the specific organisms present in the gastrointestinal tract, distinct VOC compositions or profiles are emitted from fecal matter. For example, healthy individuals have emitted VOC profiles reflecting the fact that little to no harmful bacteria or other toxins are present. However, when harmful bacterium, other harmful microorganisms, or toxins are present in the gastrointestinal tract, the VOC profile emitted from an individual's stool reflects said change. Indeed, changes in VOC profiles can indicate the occurrence or upcoming occurrence of a particular disease or harmful condition. Furthermore, for particular conditions, e.g. diaper rash, the VOC profile changes prior to the onset of visible signs of the rash. Accordingly, certain conditions or illnesses can be predicted based on VOC profiles and, in certain instances, on changes in VOC profiles. Accordingly, in embodiments, data indicative of a user's VOC profile can be analyzed via one or more processors and stored programs on the server system to provide a health status indicating health or illness. Furthermore, metadata indicative of a health state of the user can be generated. For example, data obtained from the one or more sensors can be input to a machine-learned model such that metadata is generated as an output of the machine-learned model. Such metadata can be stored on the server system and further used to analyze sensor-obtained data from the user.

At (106) the method includes providing a notification that information regarding the health state of a user is available. For example, the notification can be sent to a user via one or more devices. As noted hereinabove, the device can include a computing device 330, such as a smartphone, or can include a display device 50 on the container 10. In embodiments, upon receipt of the notification, the user can then access information regarding the health state of the user. For example, the information can include information on diseases states, such as chronic diseases or acute diseases, for which the user may be at risk. Additionally, the health state data can include information regarding the overall health and wellness of the user based on VOC profiles from their gut microbiota. In examples, where certain disease states have been identified, the user or a caretaker of the user, can then take preventative measures in order to remedy or prevent certain diseases. The notification can take a variety of forms. For instance, the notification can include a visual notification informing the user that additional data or information is available for the user to access. The notification can include audio data, e.g. a ring or chime, notifying the user that additional information is available. If delivered to a smartphone or tablet, the notification can include a vibration or other motion output capable of alerting the user.

As noted, the notification can be provided and transmitted to and displayed on a display device 50 located on a portion of the container 10. In other embodiments, it is contemplated that the notification can be transmitted to a mobile handheld device, such as a cellular phone. In embodiments, where the notification is delivered to a mobile handheld device, such as a smartphone, the user can open the notification and may access an application downloaded on the phone for reviewing additional information relating to the health state of the user. In some embodiments, the notification can be transmitted to the mobile handheld device of a user, such as a caretaker. Indeed, embodiments herein may refer to a first user and a second user. In such embodiments, the first user is the waste-generating user, such as a pediatric subject, e.g., an infant, toddler, or child, that generates waste, such as a soiled diaper. The caretaker, i.e. a second user, can include a parent, grandparent, aunt, uncle, nanny babysitter, etc. In such embodiments, the caretaker is able to review the notification and other accompanying messages and/or health information provided to make further healthcare decisions regarding the pediatric subject. While exemplary embodiments are directed to a caretaker and child relationship, the disclosure is not so limited. Indeed, a variety of caretaker situations could benefit from use of the container 10 disclosed herein. For example, the caretaker could be a healthcare worker tasked with providing in-home care for a patient suffering from Alzheimer's Disease, dementia, mental retardation, or other physical disabilities that make it difficult for the patient to care for themselves. Furthermore, while certain in-home uses are contemplated, the disclosure is not so limited. For example, the container 10 provided herein could be utilized in any clinical setting where waste capable of emitting VOCs is present and analyzation of said waste for healthcare purposes is desired.

Advantages of the containers and methods disclosed herein are numerous. For example, caretakers are able to receive pertinent, real-time information regarding their child's health, perhaps before any clinical symptoms are shown. Additionally, the containers provided are suitable for use in the home environment and allow for accurate VOC sampling in the home. Indeed, the container provided includes a unique sampling area capable of modifying the headspace environment around the waste such that accurate in-home detection is achievable. Such accurate detection and further analyzation allows for caretakers or users to obtain real-time information regarding their health status.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A waste storage device for sharing information concerning the health of a first user, the waste storage device comprising:
   a container comprising a top portion, a bottom portion, a side portion and a lid attached to the top portion of the container defining an interior space configured to receive waste;
   a sampling area formed in the interior space of the container, the sampling area configured with one or more sensors configured to detect the presence of one or more volatile organic compounds;
   a discard area disposed in the interior space, the discard area being separate from the sampling area;
   a discarding mechanism configured to move the waste from the sampling area to the discard area; and
   a server system in communication with the one or more sensors, wherein the server system is configured to deliver a notification based, at least in part, on data provided by the one or more sensors.

2. The waste storage device of claim 1, wherein the one or more sensors are configured to detect one or more volatile organic compounds in a headspace formed in the sampling area.

3. The waste storage device of claim 1, comprising a purge mechanism configured to purge the headspace of the sampling area.

4. The waste storage device of claim 1, wherein the discarding mechanism comprises a drive mechanism operably configured to move the waste to the discard area disposed in the interior of the container.

5. The waste storage device of claim 1, wherein the sampling area is located between the lid and the discarding mechanism, such that opening the lid provides access to the sampling area.

6. The waste storage device of claim 1, further comprising a staging area located between the lid and the sampling area, the staging area configured to form a sealed packet of waste material forming a headspace in the sealed packet of waste material.

7. The waste storage device of claim 1, comprising a heating element configured to heat waste in the sampling area.

8. The waste storage device of claim 1, comprising a humidity control mechanism operably configured to control relative humidity in the sampling area.

9. The waste storage device of claim 1, further comprising a display device on an exterior surface of the container, the display device configured to display the notification.

10. The waste storage device of claim 9, wherein the notification is delivered to one or more user devices.

11. The waste storage device of claim 10, wherein the one or more user devices comprises a smartphone.

12. The waste storage device of claim 10, further comprising:
   a first communication interface configured to provide communication between the one or more sensors and one or more user devices over a local network.

13. The waste storage device of claim 11, wherein the local network comprises a Bluetooth network, a Wifi network, or a cellular network.

14. The waste storage device of claim 10, further comprising a second interface configured to provide communication between the one or more sensors and one or more user devices, a server system, and combinations thereof over an external network.

15. The waste storage device of claim 14, wherein the external network comprises a Wifi network or a cellular network.

16. The waste storage device of claim 1, wherein the server system comprises a machine-learned model configured to generate metadata as an output of the machine-learned model.

17. The waste storage device of claim 1, wherein the notification alerts the user that health state data regarding the user is available.

18. The waste storage device of claim 17, wherein the health state data comprises disease state data, healthy state data, and combinations thereof.

19. The waste storage device of claim 1, wherein the waste comprises a used diaper containing urine, fecal excrement, or both worn by the first user.

* * * * *